United States Patent [19]

Tauber et al.

[11] 4,154,833

[45] May 15, 1979

[54] ANTIPHLOGISTIC PHARMACEUTICAL COMPOSITION AND METHOD OF USE

[75] Inventors: Oswald Tauber; Günther Engelhardt; Mátyás Leitold; Günther Schmidt, all of Biberach, Fed. Rep. of Germany

[73] Assignee: Boehringer Ingelheim GmbH, Ingelheim am Rhein, Fed. Rep. of Germany

[21] Appl. No.: 878,904

[22] Filed: Feb. 17, 1978

[30] Foreign Application Priority Data

Feb. 26, 1977 [DE] Fed. Rep. of Germany ....... 2708520

[51] Int. Cl.$^2$ .................... A61K 31/40; A61K 31/495
[52] U.S. Cl. ..................................... 424/250; 424/274
[58] Field of Search ................................ 424/274, 250

[56] References Cited

PUBLICATIONS

Chem. Abst. 73 - 77292m (1970).
Chem. Abst. 84 - 99253d (1976).

*Primary Examiner*—Stanley J. Friedman
*Attorney, Agent, or Firm*—Hammond & Littell

[57] ABSTRACT

Pharmaceutical compositions containing a non-steroidal anti-inflammatory compound and 5,11-dihydro-11-[(4-methyl-1-piperazinyl)-acetyl]-6H-pyrido[2,3-b]-[1,4]benzodiazepin-6-one or a non-toxic acid addition salt thereof, and a method of using the same as antiphlogistics; the pyridobenzodiazepinone ingredient effectively suppresses the gastro-intestinal side-effects of the anti-inflammatory ingredient.

2 Claims, No Drawings

ANTIPHLOGISTIC PHARMACEUTICAL COMPOSITION AND METHOD OF USE

This invention relates to novel non-ulcerogenic antiphlogistic pharmaceutical compositions containing, in combination, a non-steroidal anti-inflammatory ingredient and a pyridobenzodiazepinone.

BACKGROUND OF THE INVENTION

A number of different authors, including Katz et al. in Clin. Pharmacol. Ther. 6, 25 (1965); Bhargava et al. in Europ. J. of Pharmacol. 22, 191–195 (1973); Leonard et al. in Clin. Pharmacol. and Ther. 14 (1), 62–66 (1973); Lee et al. in Arch. Int. Pharmacodyn. 19, 370–377 (1971); and Somogyi et al. in J. Pharm. Pharmacol. 21, 122 (1969) have reported or confirmed that non-steroidal antiphlogistics produce an undersirable side-effect in that they cause gastrointestinal bleeding and lead to ulcerations of varying degrees, which often requires the discontinuance of a very necessary therapeutic treatment.

Non-steroidal antiphlogistics which are clinically used for symptomatic antiphlogistic therapy are primarily indomethacin, phenylbutazone and azapropazone. Rheumatologists are familiar with the problem of the gastro-intestinal incompatability of these symptomatic antiphlogistics, which often leads to discontinuance of or a change in the prescribed therapy. Depending upon experience, the spectrum of patients and the particular compound which is primarily used, the above described incompatabilities are encountered in 25-37% of all cases.

For want of acceptable alternatives, antacids, succus liquiritiae-preparations or carbenoxolone are, now as before, still used as a means of avoiding these side-effects.

While it is possible to achieve initial success with antacids and succus liquiritiae-preparations, their use over extended periods of time, even after a few weeks, does not provide a reliable protective effect for the mucous membrane of the gastro-intestinal tract.

The above-described undesirable side-effects can be favorably influenced with carbenoxolone, but definitive results are obtained only after long-term use. However, in 20% of the cases the long-term use of carbenoxolone produces undesirable side-effects of different types (43% edema, 36% hypokalemia, 6% hypertension); in patients above 60 years of age, these side-effects even occur in 75% of all cases.

The importance of a meaningful prophylaxis of gastrointestinal side-effects after administration of non-steroidal antiphlogistics becomes particularly significant in the case of those diseases which require life-long antiphlogistic therapy, such as Bechterew's disease and primary chronic polyarthritis. An investigation of this aspect at one of the largest rheumatism centers in the Federal Republic of Germany has shown that over a period of one year about 450 changes in therapeutic treatment per 100 patients afflicted with Bechterew's disease or primary chronic polyarthritis had to be made because of severe gastrointestinal side-effects resulting from long-term treatment with non-steroidal antiphlogistics.

OBJECTS OF THE INVENTION

It is an object of the present invention to provide antiphlogistic pharmaceutical compositions containing a nonsteroidal anti-inflammatory compound as well as a compound which effectively suppresses the undesirable gastro-intestinal side-effects of the non-steroidal anti-inflammatory agent without interfering with the desired antiphologistic activity thereof.

Other objects and advantages of the invention will become apparent as the description thereof proceeds.

DESCRIPTION OF THE INVENTION

We have discovered that the above object is achieved by antiphlogistic pharmaceutical compositions containing, in combination, a non-steroidal anti-inflammatory compound and 5,11-dihydro-11-[(4-methyl-1-piperazinyl)-acetyl]-6H-pyrido[2,3-b] [1,4] benzodiazepin-6-one (generic name: pirenzepine) or a non-toxic, pharmaceutically acceptable acid additional salt thereof, especially its dihydrochloride.

The fact that is has until now not been possible to separate the ulcerogenic side-effects of non-steroidal antiphlogistics from their desired anti-inflammatory activity (see Goodman and Gilman, *The Pharmacological Basis of Therapeutics*, 5th Ed., pages 325–358, The Macmillan Co., New York, 1975) strongly suggests that both effects must be caused by the same mechanism. Thus, our discovery, that by simultaneously administering a non-steroidal antiphlogistic and pirenzepine or a non-toxic acid addition salt thereof the gastro-intestinal side-effects are to a large extent or completely suppressed while the antiphlogistic effect is neither weakened nor antagonized, is entirely unobvious and unexpected. In fact, when administered together with pirenzepine or a non-toxic acid addition salt thereof, non-steroidal antiphlogistics can be safely administered at such high dosage levels which would otherwise not be tolerated.

For instance, we have been able to show that by administering pirenzepine dihydrochloride together with indomethacin, the so-called ulcer rate of 37% was reduced to virtually 0%. This data is based on observations made on several hundred cases over a period of two years.

Daily doses of 10 to 30 mgm have been shown in clinical tests to be sufficient to suppress the gastro-intestinal side-effects caused by all therapeutically employed nonsteroidal antiphlogistics. Based on the favorable pharmacokinetics of pirenzepine and its dihydrochloride, single therapeutic doses administered at 12-hour intervals are sufficient to assure round-the-clock mucous membrane protection.

It should also be mentioned that, under the protection of pirenzepine, it is also possible to increase the dosage of non-steroidal antiphlogistics without having to expect incompatibilities.

We have not observed any incompatibilities between pirenzepine and non-steroidal antiphlogistics.

Furthermore, we investigated by pharmacological tests to what extent pirenzepine dihydrochloride (A) produces a protective effect on the stomach of rats against the ulcerogenic effect of the following non-steroidal antiphlogistics:

(B) Indomethacin = 1-(4-chloro-benzoyl)-5-methoxy-2-methyl-1H-indole-3-acetic acid, (C) 4-[4-(2'-fluoro-biphenylyl)]-4-hydroxy-crotonic acid morpholine salt, (D) 4-(4-biphenylyl)-butanol, (E) Diclofenac = sodium [o-(2,6-dichloro-anilino)-phenyl]-acetate, (F) Naproxen = d-2-(6-methoxy-2-naphthyl)-propionic acid, (G) Phenylbutazone=4-butyl-1,2-diphenyl-3,5-pyrazolidinedione, and (H) Ibuprofen=2-(4-isobutylphenyl)-propionic acid.

In addition, we investigated whether the simultaneous administration of pirenzepine dihydrochloride weakened the acute anti-inflammatory effect of the above non-steroidal anti-phlogistics.

METHOD (1) Test for ulcerogenic effect on the stomach of the rat

The test was carried out on male and female (1:1) Chbb:THOM-rats with a body weight between 130 to 150 gm at the beginning of the study.

The test substances (non-steroidal anti-phlogistics or mixtures of these antiphlogistics with pirenzepine dihydrochloride) were administered as triturations in 1% tylose (1 ml/100 gm animal) by way of an esophageal tube once a day on three successive days.

Four hours after the last administration (i.e. on the 3rd day) the animals were killed by an over-dose of ether. The stomachs wer dissected, cut along the great curvature and washed under flowing water for subsequent macroscopic evaluation.

From the percentage of animals which, after different dosages, showed at least one stomach ulcer or one hemorrhagic erosion, using the method of LITCHFIELD and WILCOXON [J. Pharmacol. exp. Ther. 96, 99 (1949)], the $ED_{50}$ of the different non-steroidal antiphlogistics with or without the addition of pirenzepine dihydrochloride was calculated as the dose which was ulcerogenic in 50% of the animals.

(2) Test for antiphlogistic effect against the kaolininduced edema of the rat's hind paw (tested substances: A, B, C and D The test was carried out on male Chbb:THOM-rats with a body weight between 125 and 150 gm. According to HILLEBRECHT [Arzneimittel-Forsch. 4, 607 (1954)], a subplantary injection of 0.05 ml of a 10% suspension of kaolin in an aqueous 0.85% sodium chloride solution in the hind paw was used for the provocation of the kaolin edema. The other hind paw was subplantarily injected with the same volume of an aqueous 0.85% sodium chloride solution.

The measurement of the thickness of the paws was carried out using the technique of DOEPFNER and CERLETTI [Int. Arch. Allergy appl. Immunol. 12, 89 (1958)] by way of the determination of the maximum sagittal diameter, using a measuring device with constant pressure, before and 5 hours after the provocation of the edema. The test substances (the non-steroidal antiphlogistics or the mixture of non-steroidal antiphlogistics with pirenzepine dihydrochloride) were administered 30 minutes before provocation of the edema as a trituration in 1% tylose (1 ml/100 mgm animal) by way of an esophageal tube.

The diameter of the paw measured before the beginning of the test as well as the increase in diameter of the other paw caused by the injection were substracted from the diameter of the kaolin-treated paw, and this difference, being the real swelling value, was used for the further calculations.

(3) Test for antiphlogistic effect against the carrageenin-induced edema of the hind paw of the rat (test substanes: A, E, F, G and H)

The test was carried out in analogy to the above test for the kaolin-induced edema. However, the edema was induced according to the method of WINTER et al. [J. Pharmacol. 141, 369 (1963)] by subplantary injection of 0.05 ml of a 1% solution of carrageenin in an aqueous 0.85% solution of sodium chloride. The test substances (non-steroidal antiphlogistics or their mixtures with substance A) were administered 60 minutes before provocation of the edema as a trituration in 1% methyl cellulose (1 ml/100 gm animal), by way of an esophageal tube. Three hours after the provocation of the edema the measurement which provided the basis for the evaluation of an anti-exudative effect was carried out.

From the swelling values obtained by administration of different dosages of non-steroidal antiphlogistics with or without the addition of pirenzepine dihydrochloride, using a linear regression analysis according to LINDNER [Statistische Methoden, 4th Ed., pages 148–162, Birkhäuser, Basel, Switzerland (1964)], the $ED_{35}$ values of the antiphlogistics were calculated with the confidence limits according to FIELLER [Quart. J. Pharm. Pharmacol. 17, 117 (1944)], the $ED_{35}$ being the dosage which reduces the swelling of the paws by 35% in comparison to the control animals.

The following tables show the values obtained:

Table I

Effectiveness of A against the ulcerogenic effect of B, C and D in the gastro-intestinal tract of the rat after combined oral administration on 3 subsequent days.

| Antiphlogistic compound | Dosage mgm/kg | A Dosage mgm/kg | Ratio of animals with ulcers | $ED_{50}$-ulcer* mgm/kg |
|---|---|---|---|---|
| B | 2.0 | — | 4/18 | 2.55 |
| B | 2.8 | — | 11/18 | (2.16–3.01) |
| B | 4.0 | — | 16/18 | |
| B | 2.8 | 50 | 4/16 | 3.30 |
| B | 4.0 | 50 | 12/16 | (2.66–4.09) |
| B | 5.66 | 50 | 13/15 | |
| B | 2.8 | 100 | 4/16 | |
| B | 4.0 | 100 | 5/15 | 4.90 |
| B | 5.66 | 100 | 8/15 | (3.88–6.17) |
| B | 8.0 | 100 | 15/15 | |
| C | 52 | — | 5/12 | 54.5 |
| C | 62 | — | 8/12 | (47.0–63.2) |
| C | 74 | — | 10/12 | |
| C | 62 | 50 | 4/15 | |
| C | 74 | 50 | 8/17 | 83.0 |
| C | 88 | 50 | 9/17 | (70.2–98.1) |
| C | 106 | 50 | 11/17 | |
| C | 74 | 100 | 0/15 | |
| C | 88 | 100 | 4/15 | 151 |
| C | 106 | 100 | 3/15 | (117–195) |
| C | 127 | 100 | 7/15 | |
| C | 153 | 100 | 8/15 | |
| D | 28.1 | — | 4/17 | |
| D | 37.5 | — | 5/17 | 44.5 |
| D | 50.0 | — | 9/17 | (38.0–52.1) |
| D | 67.5 | — | 15/17 | |
| D | 50.0 | 50 | 1/16 | |
| D | 67.5 | 50 | 6/16 | 75.0 |
| D | 91.1 | 50 | 11/14 | (63.6–88.5) |
| D | 123.0 | 50 | 13/14 | |
| D | 50.0 | 100 | 2/16 | |
| D | 67.5 | 100 | 5/15 | 88.5 |
| D | 91.1 | 100 | 7/15 | (72.0–108.9) |
| D | 123.0 | 100 | 10/13 | |
| E | 2 | — | 5/20 | 2.95 |
| E | 4 | — | 14/20 | (2.27–3.84) |
| E | 8 | — | 19/20 | |
| E | 2 | 200 | 3/20 | 4.05 |

Table I-continued

Effectiveness of A against the ulcerogenic effect of B, C and D in the gastro-intestinal tract of the rat after combined oral administration on 3 subsequent days.

| Antiphlogistic compound | Dosage mgm/kg | A Dosage mgm/kg | Ratio of animals with ulcers | ED$_{50}$-ulcer* mgm/kg |
|---|---|---|---|---|
| E | 4 | 200 | 9/20 | |
| E | 8 | 200 | 17/19 | (2.79-5.87) |
| E | 16 | 200 | 20/20 | |
| E | 2 | 400 | 1/20 | 5.63 |
| E | 4 | 400 | 7/20 | |
| E | 8 | 400 | 13/20 | (4.02-7.88) |
| E | 16 | 400 | 19/20 | |
| F | 1.25 | — | 2/19 | 3.6 |
| F | 2.5 | — | 4/19 | |
| F | 5.0 | — | 15/19 | (2.62-4.95) |
| F | 10.0 | — | 16/19 | |
| F | 1.25 | 200 | 1/20 | 7.9 |
| F | 2.5 | 200 | 4/20 | |
| F | 5.0 | 200 | 6/20 | (5.5-11.3) |
| F | 10.0 | 200 | 10/20 | |
| F | 20.0 | 200 | 17/20 | |
| F | 1.25 | 400 | 1/20 | 10.45 |
| F | 2.5 | 400 | 0/20 | |
| F | 5.0 | 400 | 5/20 | (6.97-15.68) |
| F | 10.0 | 400 | 10/20 | |
| F | 20.0 | 400 | 14/20 | |
| G | 50 | — | 4/20 | 69.0 |
| G | 100 | — | 14/20 | |
| G | 200 | — | 20/20 | (55.6-85.6) |
| G | 50 | 200 | 2/20 | 78.0 |
| G | 71 | 200 | 8/20 | |
| G | 100 | 200 | 15/20 | (66.7-91.3) |
| G | 200 | 200 | 20/20 | |
| G | 50 | 400 | 0/20 | 138.0 |
| G | 71 | 400 | 0/20 | |
| G | 100 | 400 | 6/20 | (102.2-186.3) |
| G | 200 | 400 | 14/20 | |
| G | 400 | 400 | 18/19 | |
| H | 12.5 | — | 0/20 | 31.0 |
| H | 25 | — | 8/20 | |
| H | 50 | — | 15/20 | (23.0-41.9) |
| H | 100 | — | 19/20 | |
| H | 200 | — | 20/20 | |
| H | 25 | 100 | 6/20 | 41.5 |
| H | 50 | 100 | 11/20 | |
| H | 100 | 100 | 18/20 | |
| H | 200 | 100 | 20/20 | (29.6-58.1) |
| H | 25 | 400 | 1/20 | 52.7 |
| H | 50 | 400 | 11/20 | |
| H | 100 | 400 | 16/20 | (37.7-74.0) |
| H | 200 | 400 | 19/20 | |

*calculated according to LITCHFIELD and WILCOXON: confidence limits with 95% probability in parentheses.

Table II

Influence of A on the acute anti-exudative effect of B, C and D against the kaolin-induced edema of the hind paw of the rat, after simultaneous oral administration.

| Antiphlogistic compound | Dosage mgm/kg | A Dosage mgm/kg | n* | Thickness of the paw in $10^{-2}$ mm $\bar{x}$ | s | ED$_{35}$ mgm/kg (confidence limits) |
|---|---|---|---|---|---|---|
| Controls | — | — | 20 | 271.3 | 13.7 | |
| B | 1.5 | — | 20 | 214.8 | 21.6 | 4.3 |
| B | 3.0 | — | 19 | 189.0 | 16.5 | (3.7-5.2) |
| B | 6.0 | — | 20 | 164.5 | 18.6 | |
| Controls | — | 100 | 20 | 277.5 | 21.2 | |
| B | 1.5 | 100 | 20 | 200.3 | 19.2 | 3.0 |
| B | 3.0 | 100 | 20 | 178.3 | 19.4 | (2.5-3.6) |
| B | 6.0 | 100 | 19 | 162.9 | 15.3 | |
| Controls | — | — | 19 | 268.7 | 13.5 | |
| C | 6.25 | — | 18 | 203.9 | 22.9 | 15.3 |
| C | 12.5 | — | 19 | 179.5 | 17.0 | (13.5-17.1) |
| C | 25 | — | 20 | 164.3 | 17.9 | |
| C | 50 | — | 20 | 138.0 | 13.4 | |
| C | 100 | — | 20 | 93.8 | 17.0 | |
| Controls | — | 100 | 15 | 276.3 | 14.9 | |
| C | 6.25 | 100 | 15 | 215.6 | 24.3 | 17.6 |
| C | 12.25 | 100 | 15 | 187.0 | 21.2 | (14.4-21.5) |
| C | 25 | 100 | 15 | 166.0 | 29.5 | |
| C | 50 | 100 | 15 | 149.3 | 18.4 | |
| Controls | — | — | 45 | 269.5 | 12.5 | |
| D | 6.25 | — | 15 | 214.3 | 18.6 | 11.2 |
| D | 12 | — | 15 | 165.0 | 19.0 | (9.95-12.4) |
| D | 25 | — | 15 | 124.0 | 29.8 | |
| Controls | — | 100 | 20 | 278.0 | 14.8 | |
| D | 6.25 | 100 | 20 | 215.5 | 21.5 | 12.1 |
| D | 12 | 100 | 20 | 180.4 | 13.4 | (11.1-13.2) |
| D | 25 | 100 | 20 | 141.0 | 17.9 | |

*n = No. of animals

Table III

Influence of A on the acute anti-exudative effect of E, F, G and H, against the carrageenin-induced edema of the rat's hind paw after simultaneous administration.

| Antiphlogistic compound | Dosage mgm/kg | A Dosage mgm/kg | n* | Thickness of the paw in $10^{-2}$ mm $\bar{x}$ | s | ED$_{35}$ mgm/kg (confidence limits) |
|---|---|---|---|---|---|---|
| Controls | — | — | 20 | 278.8 | 16.4 | 51.7 |
| G | 25 | — | 19 | 216.8 | 14.8 | |
| G | 50 | — | 20 | 175.8 | 15.8 | (46.6-56.9) |

Table III-continued

Influence of A on the acute anti-exudative effect of E, F, G and H, against the carrageenin-induced edema of the rat's hind paw after simultaneous administration.

| Antiphlogistic compound | Dosage mgm/kg | A Dosage mgm/kg | n* | Thickness of the paw in $10^{-2}$ mm $\bar{x}$ | s | $ED_{35}$ mgm/kg (confidence limits) |
|---|---|---|---|---|---|---|
| G | 100 | — | 20 | 153.8 | 17.1 | |
| G | 200 | — | 20 | 125.0 | 20.2 | |
| Controls | — | 400 | 10 | 272.0 | 24.6 | 45.7 |
| G | 25 | 400 | 10 | 205.0 | 27.0 | |
| G | 50 | 400 | 10 | 173.5 | 21.9 | (36.6–55.9) |
| G | 100 | 400 | 9 | 138.9 | 25.8 | |
| Controls | — | — | 10 | 267.0 | 22.9 | 39.6 |
| H | 20 | — | 10 | 210.0 | 28.2 | |
| H | 40 | — | 10 | 167.0 | 16.2 | (33.6–45.9) |
| H | 80 | — | 10 | 141.5 | 15.8 | |
| Controls | — | 400 | 10 | 272.0 | 24.6 | 34.2 |
| H | 20 | 400 | 10 | 204.0 | 18.5 | |
| H | 40 | 400 | 10 | 170.0 | 21.5 | (28.8–39.7) |
| H | 80 | 400 | 9 | 131.7 | 22.6 | |
| Controls | — | — | 10 | 267.0 | 22.9 | 2.8 |
| F | 2 | — | 10 | 188.5 | 11.1 | |
| F | 4 | — | 10 | 157.5 | 13.2 | (2.3–3.2) |
| F | 8 | — | 10 | 118.0 | 24.6 | |
| Controls | — | 400 | 10 | 272.0 | 24.6 | 3.0 |
| F | 2 | 400 | 9 | 192.2 | 28.2 | |
| F | 4 | 400 | 10 | 168.5 | 20.0 | (2.2–3.7) |
| F | 8 | 400 | 9 | 133.3 | 19.7 | |
| Controls | — | — | 10 | 271.0 | 18.2 | 5.0 |
| E | 1.5 | — | 10 | 209.5 | 19.4 | |
| E | 3 | — | 10 | 188.5 | 12.9 | (4.1–6.1) |
| E | 6 | — | 10 | 170.0 | 16.5 | |
| E | 12 | — | 10 | 154.0 | 13.3 | |
| Controls | — | 400 | 10 | 271.0 | 18.3 | 4.3 |
| E | 1.5 | 400 | 10 | 209.5 | 15.9 | |
| E | 3.0 | 400 | 10 | 181.5 | 12.0 | (3.4–5.0) |
| E | 6.0 | 400 | 10 | 162.5 | 17.2 | |
| E | 12.0 | 400 | 10 | 148.5 | 21.9 | |

*n = No. of animals

Results

By virtue of the addition of pirenzepine dihydrochloride (substance A), the $ED_{50}$ for ulcerogenicity of the tested antiphlogistics in the stomach of the rat undergoes a dosedependent increase (see table I). The simultaneous oral administration of pirenzepine dihydrochloride, on the other hand, does not lead to a reduction of the acute anti-exudative effect of non-steroidal antiphlogistics on the kaolin- and carrageenin-induced edema of the rat (see tables II and III).

By means of substance A the ulcerogenic effect of nonsteroidal antiphlogistics in the stomach of the rat can be weakened in dose-dependent manner. Since the acute antiexudative effect of these non-steroidal antiphlogistics is not reduced by the simultaneous administration of substance A, this anti-ulcerogenic effect of A cannot be caused by a direct interaction with the tested non-steroidal antiphlogistics or by a reduction of their absorption.

The results prove that 5,11-dihydro-11-[(4-methyl-1-piperazinyl) acetyl]-6H-pyrido[2,3-b] [1,4]benzodiazepin-6-one or its non-toxic, pharmaceutically acceptable acid addition salts formed with inorganic or organic acids are able to abolish the gastro-intestinal side-effects (formation of lesions, hemorrhagias and formation of ulcers) of nonsteroidal antiphlogistics, while the antiphlogistic activity of these antiphlogistics is fully retained.

The antiphlogistic pharmaceutical compositions according to this invention are characterized in that they contain as an active ingredient any desired non-steroidal antiphlogistic compound or a non-toxic, pharmaceutically acceptable salt thereof in combination with 5,11-dihydro-11-[(4-methyl-1-piperazinyl) acetyl]-6H-pyrido[2,3-b] [1,4] benzodiazepin6-one or a non-toxic, pharmaceutically acceptable salt thereof formed with inorganic or organic acids, where the dosage ratio of the pyridobenzodiazepinone to the antiphlogistic is in the range of 1:500 to 1:2, depending upon the effective strength of the antiphlogistic.

In general, the daily does rate of 5,11-dihydro-11[(4-methyl-1-piperazinyl) acetyl]-6H-pyrido [2,3-b] [1,4] benzodiazepin-6-one or of a non-toxic acid addition salt thereof is between 0.16 to 0.83 mgm/kg. The novel compositions may also contain other pharmacologically effective compounds and/or inert carriers and/or excipients conventionally used in pharmaceutical compositions.

The following known compounds can be used as antiphlogistic components for the compositions of the present invention:

0-acetyl-salicylic acid,
Flufenisal = 2-(acetyloxy)-5-(4-fluoro-phenyl)-benzoic acid,
Diflunisal = 2-(hydroxy)-5-(2,4-difluoro-phenyl)-benzoic acid,
Ibuprofen = 2-(4-isobutyl-phenyl)-propionic acid,
Indomethacin = 1-(4-chloro-benzoyl)-5-methoxy-2-methyl-1H-indole-3-acetic acid,
Ketoprofen = 2-(3-benzoyl-phenyl)-propionic acid,
Suprofen = α-methyl-4-[(2-thienyl)carbonyl]-benzene-acetic acid, Tolmetin=1-methyl-5-(p-toluoyl)-pyrrol-2-acetic acid and its salts, mainly the 1-methyl-5-(p-toluoyl)pyrrol-2-acetic acid sodium salt dihydrate, Sulindac=Z-5-fluoro-2-methyl-1(4-methylsulfinyl-benzylidene)-indene-3-acetic acid, Flurbiprofen=2-(2-fluoro-4-biphenylyl)-propionic acid, Naproxen=(+)-6-methoxy-α-methyl-2-naphthaleneacetic acid, Fenoprofen=2-(3-phenoxy-phenyl)-propionic acid and its salts, mainly the 2-(3-phenoxy-phenyl)-propionic acid calcium salt dihydrate, 6-Chloro-α-methyl-carbazole-2-acetic acid, Fenbufen=4-(4-biphenylyl)-4-oxo-butyric acid, Bucloxinic acid=4-(3-chloro-4-cyclohexyl-phenyl)-4-oxo-butyric-acid, 6,11-Dihydro-11-oxo-dibenz [b,e] oxepine-2-acetic acid, d-2-(6,11-Dihydro-11-oxo-dibenzo[b,e]thiepin-3-yl)-propionic acid and its non-toxic pharmaceutically acceptable salts formed with inorganic and organic bases, d-2-(6,11-Dihydro-11-oxo-dibenzo[b,e]oxepin-3-yl)-propionic acid and its non-toxic, pharmaceutically acceptable salts formed with inorganic and organic bases, d-α-methyl-5-oxo-5H-dibenzo[a,d]cycloheptene-2-acetic acid and its non-toxic, pharmaceutically acceptable salts formed with inorganic and organic bases, Etodolic acid=1,8-diethyl-1,3,4,9-tetrahydro-pyrano[3,4-b] indole-2-acetic acid, E-4-(2-fluoro-4-biphenylyl)-4-hydroxy-2-butenic acid, 4-(4-biphenylyl)-1-butanol, Diclofenac=o-[(2,6-dichloro-phenyl)amino]-phenylacetic acid and its non-toxic, pharmaceutically acceptable salts formed with inorganic and organic bases, mainly sodium [o-[(2,6-dichlorophenyl)amino]-phenyl]acetate, Flufenamic acid=2-[[3-(Trifluoromethyl)phenyl]amino]-benzoic acid, Meclofenamic acid=2-[(2,6-dichloro-3-methyl-phenyl)amino]-benzoic acid and its non-toxic, pharmaceutically acceptable salts formed with inorganic and organic bases, mainly the sodium salt, Mefenamic acid=2-[(2,3-dimethyl-phenyl)amino]-benzoic acid, Niflumic acid 2{[3-(trifluoromethyl)phenyl]amino}-3-pyridine-carboxylic acid, Phenylbutazone=4-(1-butyl)-1,2-diphenyl-3,5-dioxopyrazolidine and its non-toxic, pharmaceutically acceptable salts formed with inorganic and organic bases, mainly the sodium salt, Pyrazinobutazone=equimolecular salt of phenylbutazone and piperazine, Oxyphenbutazone=4-(1-butyl)-1-(4-hydroxy-phenyl)-2-phenyl-3,5-dioxo-pyrazolidine, 1,4-diphenyl-3,5-dioxo-pyrazolidine and its non-toxic, pharmaceutically acceptable salts formed with inorganic and organic bases, Feprazone=4-(3-methyl-2-buten-1-yl)-1,2-diphenyl-3,5-pyrazolidindione, Azapropazone=5-dimethylamino-9-methyl-2-propyl-1H-pyrazolo[1,2-a] [1,2,4]benzotriazine-1,3(2H)-dione, Bumadizone calcium semihydrate=butylmalonic acid mono-(1,2-diphenyl)-hydrazide calcium salt semihydrate, Sudoxicam=4-hydroxy-2-methyl-N-(2-thiazolyl)-2H-1,2-benzothiazine-3-carboxamide-1,1-dioxide, Piroxicam=4-hydroxy-2-methyl-N-(2-pyridyl)-2H-1,2-benzothiazine-3-carboxamide-1,1-dioxide, Isoxicam=4-hydroxy-2-methyl-N-(5-methyl-3-isoxazolyl)-2H-1,2-benzothiazine-3-carboxamide-1,1-dioxide, 4-Hydroxy-2-methyl-N-(2-thiazolyl)-2H-naphtho[2,1-e]-1,2-thiazine-3-carboxamide-1,1-dioxide, Proquazone=7-methyl-4-phenyl-1-(2-propyl)-2(1H)-quinazolinone, Flumizol=4,5-bis-(4-methoxy-phenyl)-2-(trifluoromethyl)imidazole, and E-{[(p-chloro-α-methyl-benzylidene)amino]oxy}-acetic acid 2-(dimethylamino) ethyl ester hydrochloride.

The present invention also relates to the process for the preparation of the pharmaceutical compositions according to this invention, which comprises combining any non-steroidal antiphlogistic compound or a non-toxic, pharmaceutically acceptable salt thereof with 5,11-dihydro-11[(4-methyl-1-piperazinyl)acetyl]-6H-pyrido[2,3-b] [1,4] benzodiazepin-6-one or a non-toxic, pharmaceutically acceptable acid addition salt thereof in the proportion pyridobenzodiazepinone to antiphlogistic from 1:500 to 1:2, and formulating the combination, optionally with other known active ingredients, with customary carriers and/or excipients into tablets, coated pills, powders, syrups, capsules, effervescent tablets, suppositories or the like.

The pharmaceutical compositions according to this invention are administered orally, rectally and/or parenterally, once daily or in several smaller doses. The preparation of the tablets, coated pills, suppositories, powder mixtures and syrups is performed in known manner; for instance, the tablets are produced by directly compressing a mixture of the active ingredients and the excipients, and the tablets can subsequently optionally be coated with a film which is soluble in the stomach and gastro-intestinal tract. For the preparation of capsules, the mixture of active ingredients and excipients is filled into capsules made of hard gelatin, for example. The carrier substances in the suppositories are vegetable fats for instance hardened vegetable oil or triglycerides of fatty acids with 12 to 18 carbon atoms, and the active ingredients combination is homogeneously distributed therein.

The following examples illustrate the present invention and will enable others skilled in the art to understand it more completely. It should be understood, however, that the invention is not limited solely to the particular examples given below.

EXAMPLE 1

Effervescent tablets with pirenzepine-dihydrochloride and ascorbic acid

The tablet composition is compounded from the following ingredients:

| | |
|---|---|
| Pirenzepine dihydrochloride | 10.0 parts |
| Ascorbic acid | 200.0 parts |
| Citric acid, anhydrous | 1060.0 parts |
| Sodium bicarbonate | 1670.0 parts |
| Sodium benzoate | 40.0 parts |
| Polyvinylpyrrolidone | 20.0 parts |
| Total | 3000.0 parts |

Preparation:

The pirenzepine dihydrochloride, the ascorbic acid, the citric acid and the sodium bicarbonate are mixed together, and the mixture is moistened with a 10% solution of polyvinylpyrrolidone in ethanol. The moist mass is then granulated and dried at a temperature of 45° C. The dry granulate is admixed with the sodium benzoate, and the composition is compressed into 3000 mgm-tablets. The tablets must be prepared in an air-conditioned room in which the relative humidity is kept below 30%. Each tablet contains 10 mgm of pirenzepine dihydrochloride and 200 mgm of ascorbic acid.

EXAMPLE 2

Tablets with microencapsuled acetylsalicylic acid and pirenzepine dihydrochloride The tablets are compounded from the following ingredients:

| | |
|---|---|
| Acetylsalicylic acid, microencapsuled | 500.0 parts |
| Pirenzepine dihydrochloride | 10.0 parts |
| Lactose | 50.0 parts |
| Corn starch | 48.0 parts |
| Stearic acid | 4.0 parts |
| Polyvinylpyrrolidone | 8.0 parts |
| Total | 620.0 parts |

Preparation:

The acetylsalicylic acid, the pirenzepine dihydrochloride, the lactose and the corn starch are mixed together, and the mixture is moistened with an aqueous 10% solution of polyvinylpyrrolidone in which the stearic acid is dissolved by heating. The moist mass is then granulated and dried at a temperature of 45° C. The dry granulate is compressed into 620 mgm-tablets. Each tablet contains 500 mgm aspirin and 10 mgm pirenzepine dihydrochloride.

EXAMPLE 3

Stomach juice-resistant coated tablets with sodium o-[(2,6-dichloro-phenyl)amino]-phenylacetate and pirenzepine dihydrochloride The tablets are compounded from the following ingredients:

| | |
|---|---|
| sodium 0-[(2,6-dichloro-phenyl)-amino]-phenyl-acetate | 75.0 parts |
| Pirenzepine dihydrochloride | 5.0 parts |
| Calcium phosphate | 120.0 parts |
| Corn starch | 50.0 parts |
| Soluble starch | 8.0 parts |
| Magnesium stearate | 2.0 parts |
| Total | 260.0 parts |

Preparation:

The sodium o-[(2,6-dichloro-phenyl)amino]-phenylacetate, the pirenzepine dihydrochloride, the calcium phosphate and the corn starch are intimately admixed, and moistened with an aqueous 20% solution of the soluble starch. The moist mixture is then granulated through a screen and dried at a temperature of 45° C. The dry granulate is admixed with the magnesium stearate and compressed into 260 mgm-tablets. Subsequently, the tablets are coated with a mixture consisting of anionic polymerizates of methacrylic acid and methacrylates dissolved in an acetone/isopropanol mixture. The coated tablets are then provided in known manner with a thin outer shell consisting of sugar and talcum. The finished coated tablets are polished with beeswax. Each coated tablet contains 75 mgm of sodium o-[(2,6-dichloro-phenyl)-amino]-phenylacetate and 5 mgm of pirenzepine dihydrochloride.

EXAMPLE 4

Coated tablets with phenylbutazone and pirenzepine dihydrochloride

The tablets are compounded from the following ingredients:

| | |
|---|---|
| Pirenzepine dihydrochloride | 10.0 parts |
| Phenylbutazone | 200.0 parts |
| Lactose | 93.5 parts |
| Corn starch | 50.0 parts |
| Cellulose, microcrystalline | 40.0 parts |
| Polyvinylpyrrolidone | 5.0 parts |
| Magnesium stearate | 1.5 parts |
| Total | 400.0 parts |

Preparation:

The active ingredients are admixed with the lactose, the corn starch and the cellulose, and the mixture is moistened with a 10% solution of the polyvinylpyrrolidone in water. The mass is then granulated and dried at a temperature of 45° C., and the dry granulate is admixed with the magnesium stearate. The mixture is then compressed into 400mgm-tablets which are subsequently coated with a thin shell consisting essentially of sugar and talcum. The coated tablets are polished with beeswax. Each coated tablet contained 100 mgm of phenylbutazone and 10 mgm of pirenzepine dihydrochloride.

EXAMPLE 5

Coated tablets with 1-(4-chloro-benzoyl)-5-methoxy-2-methyl-1H-indole-3-acetic acid and pirenzepine dihydrochloride The tablets are compounded from the following ingredients:

| | |
|---|---|
| Pirenzepine dihydrochloride | 5.0 parts |
| 1-(4-chloro-benzoyl)-5-methoxy-2-methyl-1H-indole-3-acetic acid | 50.0 parts |
| Lactose | 75.0 parts |
| Corn starch | 34.0 parts |
| Gelatin | 10.0 parts |
| Carboxy methyl cellulose | 5.0 parts |
| Magnesium stearate | 1.0 parts |
| Total | 180.0 parts |

Preparation:

An intimate mixture of the active ingredients, the corn starch and the lactose is moistened with an aqueous 75% solution of the gelatin, the moist mass is granulated through a 1.5 mm-mesh screen and dried at a temperature of 45° C. The dry granulate is then admixed with the carboxy methyl cellulose and the magnesiumstearate, and the composition is compressed into 180 mgm-tablets which are then coated with a thin shell consisting essentially of sugar and talcum. The coated tablets are polished with beeswax. Each coated tablet contains 50 mgm of the indole compound and 5 mgm of pirenzepine dihydrochloride.

EXAMPLE 6

Suppositories with
1-(4-chloro-benzoyl)-5-methoxy-2-methyl1H-indole-3-acetic acid and pirenzepine dihydrochloride The suppositories are compounded from the following ingredients:

| | | |
|---|---|---|
| 1-(4-Chloro-benzoyl)-5-methoxy-2-methyl-1H-indole-3-acetic acid | 100 | parts |
| Pirenzepine dihydrochloride | 25 | parts |
| Suppository base (e.g. cocoa butter) | 1575 | parts |
| Total | 1700 | parts |

Preparation:

After melting the suppository base, the active ingredients are homogeneously suspended therein at 40° C. by intensive stirring. 1700 mgm-portions of the composition are poured into slightly pre-cooled suppository moulds and allowed to harden therein. Each suppository contains 100 mgm of the indole compound and 25 mgm of pirenzepine dihydrochloroide.

EXAMPLE 7

Suppositories with
4-(1-butyl)-1,2-diphenyl-3,5-dioxo-pyrazolidine and pirenzepine dihydrochloride The suppositories are compounded from the following ingredients:

| | | |
|---|---|---|
| 4-(1-butyl)-1,2-diphenyl-3,5-dioxo pyrazolidine | 250 | parts |
| Pirenzepine dihydrochloride | 25 | parts |
| Suppository base (e.g. cocoa butter) | 1425 | parts |
| Total | 1700 | parts |

Preparation:

After melting the suppository base, the active ingredients are homogeneously suspended therein at 40° C. by intensive stirring. 1700 mgm-portions of the composition are poured into slightly pre-cooled suppository moulds and allowed to harden therein. Each suppository contains 250 mgm of the pyrazolidine compound and 25 mgm of pirenzepine dihydrochloride.

EXAMPLE 8

Ampules

The dry substance ampule contains:

| | |
|---|---|
| Pirenzepine dihydrochloride | 10 mgm |
| Mannitol | 50 mgm |

The solution ampule contains:

| | | |
|---|---|---|
| 4-(1-butyl)-1,2-diphenyl-3,5-dioxo-pyrazolidine | | 450 mgm |
| Aminophenazone | | 450 mgm |
| Lidocaine | | 35 mgm |
| Sodium hydroxide | | 55 mgm |
| Distilled water | ad. | 3.0 ml |

Preparation:

The pirenzepine dihydrochloride is, together with the mannitol, dissolved in ampule water; 1 ml-portions of the solution are filled into 5 ml-injection bottles and lyophilized according to known methods.

For parenteral administration, the contents of an ampule with the dry substances and the contents of a solution ampule, which comprises the antiphlogistics and the local anaesthetic, are combined and immediately injected thereafter.

EXAMPLE 9

Soluble Granulate

Composition of the granulate:

| | | |
|---|---|---|
| Acetylsalicylic acid | 5.0 | parts |
| Pirenzepine dihydrochloride | 0.1 | parts |
| Sodium benzoate | 0.2 | parts |
| Citric acid | 0.1 | parts |
| Yellow-orange 11963 | 0.006 | parts |
| Sugar | 19.094 | parts |
| Karion instant | 15.0 | parts |
| Satiagum | 0.25 | parts |
| Banana 54330 | 0.2 | parts |
| Caramel 52929 | 0.05 | parts |
| Total | 40.000 | parts |

The ingredients are well pulverized and admixed, and the mixture is filled in suitable bottles.

40 gm of the soluble granulate are dissolved in 100 ml of water before use. The solution contains 5 gm of aspirin and 0.1 gm of pirenzepine dihydrochloride.

EXAMPLE 10

Gelatin capsule with inserted core

| Capsule ingredients: | mgm capsule |
|---|---|
| Acetylsalicylic acid, crystalline | 330.0 |
| Pirenzepine dihydrochloride | 10.0 |
| Corn starch, dried | 78.0 |
| Lactose, pulverized | 10.0 |
| Aluminum stearate | 2.0 |
| | 430.0 |
| Ingredients of the core: | |
| 2,6-bis (diethanolamino)-4,8-diperidino-pyrimido [5,4-d]pyrimidine | 75.0 mgm |
| Polyvinylpyrrolidone K 30 | 2.5 mgm |
| Formaldehyde gelatin | 6.5 mgm |
| Magnesium stearate | 1.0 mgm |
| Coating: | |
| Talcum | about 13.4 mgm |
| Sugar | about 4.2 mgm |
| Gum arabic | about 2.4 mgm |
| Core + coating | 105.0 mgm |

The ingredients of the capsule are ground, mixed and filled into gelatine capsules; subsequently, by means of an appropriate machine, the core consisting of the above mentioned ingredients is put into the capsule, and the capsule was closed. The core is compressed and coated in the usual way. Each capsule contains 75 mgm of 2,6-bis (diethanolamino)-4,8-dipiperidino-pyrimido[5,4-d]pyrimidine, 330 mgm of acetylsalicylic acid and 10 mgm of pirenzepine dihydrochloride. While the present invention has been illustrated with the aid of certain specific embodiments thereof, it will be readily apparent to others skilled in the art that the invention is not limited to these particulare embodiments, and that various changes and modifications may be made without departing from the spirit of the invention or the scope of the appended claims.

We claim:

1. The method of suppressing the undesirable gastrointestinal side-effects produced by administering an effective antiphlogistic amount of 1-(4-chloro-benzoyl)-5-methoxy-2-methyl-1H-indole-3-acetic acid to a warm-blooded animal in need thereof, which comprises simultaneous administering to said animal 1 part by weight of 5,11-dehydro-11-[(4-methyl-1-piperazinyl)-acetyl]-6H-pyrido[2,3-b][1,4]-benzodiazepin-6-one per 2 to 500 parts by weight of 1-(4-chloro-benzoyl)-5-methoxy-2-methyl-1H-indole-3-acetic acid.

2. An antiphlogistic pharmaceutical composition consisting essentially of an inert pharmaceutical carrier, an effective antiphlogistic amount of 1-(4-chloro-benzoyl)-5-methoxy-2-methyl-1H-indole-3-acetic acid, and 5,11-dihydro-11-[(4-methyl-1-piperazinyl)-acetyl]-6H-pyrido[2,3-b][1,4]-benzodiazepin-6-one or a non-toxic, pharmaceutically acceptable acid addition salt thereof, where the weight ratio of 5,11-dihydro-11-[(4-methyl-1-piperazinyl)-acetyl]-6H-pyrido[2,3-b][1,4]benzodiazepin-6-one or a non-toxic, pharmaceutically acceptable acid addition salt thereof to 1-(4-chlorobenzoyl)-5-methoxy-2-methyl-1H-indole-3-acetic acid is within the range of 1:500 parts to 1:2 parts.

* * * * *

UNITED STATES PATENT AND TRADEMARK OFFICE
CERTIFICATE OF CORRECTION

PATENT NO. : 4,154,833                    Page 1 of 2
DATED     : May 15, 1979
INVENTOR(S) : OSWALD TAUBER ET AL.

It is certified that error appears in the above-identified patent and that said Letters Patent are hereby corrected as shown below:

Column 1, line 17: "undersirable" should read -- undesirable --

Column 3, line 37: Between "kaolin" and "induced", there should be a hyphen --  -  --;
        line 38: After "D", there should be a parenthesis -- ) --;

Column 7, line 40: Between "dose" and "dependent", there should be a hyphen --  -  --;

Column 8, line 40: Between "benzodiazepin" and "6", there should be a hyphen --  -  --;

Column 9, line 39: After "phenyl", there should be -- ] --;
        line 40: "]", first occurrence, should be cancelled;
        line 41: After "phenyl", there should be -- ) --;
        line 42: ")" before "amino" should be cancelled;
        line 48: After "Niflumic acid" there should be -- = --
        line 50: "diox-" should read -- dioxo-  --;
        line 51: "opyrazolidine" should read -- pyrazolidine --;

Column 11, line 47: After "amino]-phenyl-acetate" cancel "5.0 parts";
Thereafter please insert the following line" -- Pirenzepine dihydrochloride    5.0 parts--;

Column 13, line 4: Between "methyl" and "1H", there should be a hyphen --  -  --;

Column 15, line 9: The text  "While certain specific .....

UNITED STATES PATENT AND TRADEMARK OFFICE
CERTIFICATE OF CORRECTION

PATENT NO. : 4,154,833      Page 2 of 2

DATED : May 15, 1979

INVENTOR(S) : OSWALD TAUBER ET AL.

It is certified that error appears in the above-identified patent and that said Letters Patent are hereby corrected as shown below:

"....scope of the appended claims."
should be a separate paragraph.

Signed and Sealed this

Eighteenth Day of December 1979

[SEAL]

Attest:

SIDNEY A. DIAMOND

Attesting Officer      Commissioner of Patents and Trademarks